US012660997B2

(12) United States Patent (10) Patent No.: US 12,660,997 B2
St. John et al. (45) Date of Patent: Jun. 23, 2026

(54) SYSTEM AND METHOD FOR DYNAMIC OPTICAL CONTRAST IMAGING

(71) Applicant: The Regents of the University of California, Oakland, CA (US)

(72) Inventors: Maie A. St. John, Oakland, CA (US); Peter Andras Pellionisz, Mountain View, CA (US); Oscar M. Stafsudd, Oakland, CA (US); Yong Hu, Beijing (CN)

(73) Assignee: The Regents of the University of California, Oakland, CA (US)

( * ) Notice: Subject to any disclaimer, the term of this patent is extended or adjusted under 35 U.S.C. 154(b) by 619 days.

(21) Appl. No.: 17/997,087

(22) PCT Filed: Apr. 29, 2021

(86) PCT No.: PCT/US2021/029975
§ 371 (c)(1),
(2) Date: Oct. 25, 2022

(87) PCT Pub. No.: WO2021/222629
PCT Pub. Date: Nov. 4, 2021

(65) Prior Publication Data
US 2023/0218154 A1 Jul. 13, 2023

Related U.S. Application Data

(60) Provisional application No. 63/017,558, filed on Apr. 29, 2020.

(51) Int. Cl.
*A61B 5/00* (2006.01)
*A61B 1/04* (2006.01)
*A61B 1/06* (2006.01)

(52) U.S. Cl.
CPC ............ *A61B 1/0684* (2013.01); *A61B 1/043* (2013.01)

(58) Field of Classification Search
CPC ..... A61B 1/0684; A61B 1/043; A61B 5/0071; G01N 2201/062; G01N 21/6458; G01N 21/6408
See application file for complete search history.

(56) References Cited

U.S. PATENT DOCUMENTS

2006/0149479 A1* 7/2006 Ma ............................ G06T 5/94
382/128
2015/0053871 A1 2/2015 Grundfest et al.
(Continued)

FOREIGN PATENT DOCUMENTS

WO 2013131062 A1 9/2013
WO 2015195975 A1 12/2015
WO 2019089998 A1 5/2019

OTHER PUBLICATIONS

Cheng, H. et al., Dynamic Optical Contract Imaging (DOCI): System Theory for Rapid, Wide-Field, Multispectral Optical Imaging Using Fluorescence Lifetime Contrast Mechanism, Proc. of SPIE, 2019, vol. 10951, pp. 1-16.
Papour, A., Fast Biomedical Imaging Using Fluorescence Lifetime and Unique Raman Signatures, Dissertation, University of California, Los Angeles, 2015, 85 pages.
(Continued)

*Primary Examiner* — May A Abouelela
(74) *Attorney, Agent, or Firm* — Quarles & Brady LLP

(57) ABSTRACT
A method for imaging tissue is provided. The method includes illuminating a target tissue via a light-emitting diode. The method further includes acquiring a plurality of timed images of the target tissue including an excitation image corresponding to an excitation state of the light-emitting. Additionally, the method includes generating a relative lifetime map of the target tissue based on the plurality of timed images.

21 Claims, 11 Drawing Sheets

(56)  References Cited

U.S. PATENT DOCUMENTS

| | | | |
|---|---|---|---|
| 2019/0003969 A1* | 1/2019 | Jovin | G01N 21/6486 |
| 2019/0296521 A1* | 9/2019 | Yun | H01S 5/36 |
| 2020/0070166 A1* | 3/2020 | Skala | G01N 15/1459 |
| 2020/0121245 A1* | 4/2020 | Barclay | A61B 5/7275 |
| 2020/0132976 A1* | 4/2020 | Ameer-Beg | G02B 21/0036 |
| 2020/0292457 A1* | 9/2020 | Hassibi | G01J 3/4406 |
| 2020/0323431 A1* | 10/2020 | St. John | A61B 5/444 |
| 2021/0164905 A1* | 6/2021 | B. Nieder | G02B 21/0032 |
| 2021/0389244 A1* | 12/2021 | Bowman | G01S 17/894 |
| 2021/0404964 A1* | 12/2021 | Schwedt | G02B 21/008 |
| 2022/0034809 A1* | 2/2022 | Hayakawa | G06N 20/00 |
| 2022/0104706 A1* | 4/2022 | Dacosta | A61B 5/0071 |

OTHER PUBLICATIONS

Pellionisz, P. et al., Ratiometric Autofluorescence Lifetime Imaging System Standardization and Application for Head and Neck Cancer, Proc. of SPIE, 2019, vol. 11190, pp. 1-8.

Sherman, A. et al., Normalized Fluorescence Lifetime Imaging for Tumor Identification and Margin Delineation, Proc. of SPIE, 2013, vol. 8572, pp. 1-14.

Tajudeen, B. et al., Dynamic Optical Contrast Imaging as a Novel Modality for Rapidly Distinguishing Head and Neck Squamous Cell Carcinoma from Surrounding Normal Tissue, Cancer, 2017, 123(5):879-886.

PCT International Search Report and Written Opinion, PCT/US2021/029975, Aug. 20, 2021, 9 pages.

European Patent Office, Extended Search Report, Application No. 21796782.7, Mar. 25, 2024, 10 pages.

* cited by examiner

40

GATED IMAGE INDEX

70

76

| DYE | SOLVENT | CONCENTRATION (uM) | LIFETIME (ns) | DOCI VALUE (0-1) |
|---|---|---|---|---|
| 7-HYDROXY-4-METHYLCOUMARIN | DISTILLED WATER | 400 | 5.229 | 0.8556 |
| | | 260 | 5.243 | |
| LAURDAN | METHANOL | 1000 | 3.143 | |
| | | 650 | 3.106 | 0.7653 |
| | | 430 | 3.172 | |
| NADH | DISTILLED WATER | 21500 | 0.397 | 0.6280 |
| | | 14500 | 0.417 | |

Acquire a background image of a target tissue — 88

Activate a light-emitting diode — 90

Acquire an excitation image of the target tissue — 92

Acquire a calibration image of the target tissue — 94

Acquire a decay image of the target tissue — 96

Calculate a total signal image — 98

100

| Illuminate a target tissue via a light-emitting diode | 102 |

| Acquire a plurality of timed images of the target tissue | 104 |

| Generate a relative lifetime map of the target tissue | 106 |

SYSTEM AND METHOD FOR DYNAMIC OPTICAL CONTRAST IMAGING

CROSS-REFERENCE TO RELATED APPLICATIONS

The present application represents the national stage entry of PCT/PCTUS2021/029975 filed on Apr. 29, 2021 and relates to and claims priority from U.S. Provisional Patent Application Ser. No. 63/017,558 filed Apr. 29, 2020, the disclosure of which is incorporated herein by reference in its entirety.

STATEMENT REGARDING FEDERALLY SPONSORED RESEARCH

This invention was made with government support under Grant Numbers CA220663 and CA205051 awarded by the National Institutes of Health. The government has certain rights in the invention.

BACKGROUND

The present disclosure generally relates to medical imaging, and more particularly to signal detection levels in a Dynamic Optical Contrast Imaging (DOCI) system.

Biomedical imaging has become an indispensable tool in comprehensive cancer surgery. While some aims are much closer to full realization, continuing advances in biomedical photonics may help detect pre-malignant lesions, detect cancer in less invasive stages, reduce the number of unnecessary biopsies, and also provide guidance towards the complete tumor removal with precise resection margins. Surgeons must accurately determine tumor margins intraoperatively to minimize over/under resection. This can result in: (a) under-resection (positive margins), which increases risk for disease recurrence; or (b) over-resection (excessive negative margins), which can affect long-term patient outcomes. The surgeon's fingertips (i.e. palpation) are often cited as the "gold standard" for intraoperative margin assessment. However, palpation is inherently subjective to each surgeon's touch. Intraoperative guidance with X-ray, ultrasound, and MRI are certainly feasible, yet limitations exist in the widespread integration of these imaging modalities. For example, the principle use of such tools remains in the preoperative localization of many larger tumors (e.g., oral, liver, lung, kidney, brain).

The application of such tools can be especially challenging in the area of head and neck surgery, due to the high density and proximity of delicate anatomy (e.g., carotid artery and recurrent laryngeal nerve) to areas frequently undergoing operation. As an example, intraoperative localization and detection involving head and neck squamous cell carcinoma (HNSCC) and oral squamous cell carcinoma (OSCC) can be difficult.

Despite ongoing research in endoscopic and laparoscopic technologies in the surgical management of patients with OSCC, the 5-year survival rate among this patient cohort (~50%) has only marginally improved over the past three decades. Within the United States alone, approximately 13,800 OSCC cases reoccur per year, and depending on the tumor site, reoccurrence rates associated with positive margins may range from 25%-50%. In comparison, local recurrence rates in patients with tumor-free margins are reported to be 3.9%. Tumors of the head and neck region are unique given their close vicinity to vital structures, including the cranial nerves and carotid arteries. The success of oncologic head and neck surgery, thus, heavily depends on the sensitivity with which tumor and vital tissue can be intraoperatively detected.

In light of the above, there is a need for improved systems and methods for intraoperative surgical guidance and margin assessment.

SUMMARY

The present disclosure includes a system for intraoperative imaging. The system includes a camera, a light-emitting diode, and a processor in communication with the camera and the light-emitting diode. The processor is configured to illuminate a target tissue via the light-emitting diode. The processor is further configured to acquire, via the camera, a plurality of timed images of the target tissue including an excitation image corresponding to an excitation state of the light-emitting diode and a decay image corresponding to a decay state of the light-emitting diode. Additionally, the processor is configured to generate a relative lifetime map of the target tissue based on the plurality of timed images.

In some embodiments, the plurality of timed images includes a calibration image and a background image. The calibration image can correspond to a steady-state of the light-emitting diode, and the background image can correspond to an average detected signal when the light-emitting diode is not illuminated. Additionally, in some embodiments, the excitation state of the light-emitting diode occurs for 1 to 10 nanoseconds. In some embodiments, the processor can acquire the plurality of timed images in the presence of background lighting. Additionally, in some embodiments, the processor can acquire the plurality of timed images and generate the relative lifetime map in real-time. In some embodiments, the relative lifetime map can include a boundary on the target tissue, the boundary identifying cells having a first property from cells having a second property. The first property can correspond to cells having a first physiologic process and the second property can correspond to cells having a second physiologic process. The system can further include a user display in communication with the processor, and the processor can be further configured to output the relative lifetime map to the user display. In some embodiments, the processor can be configured to illuminate and acquire the plurality of timed images of in-vivo tissue.

The present disclosure additionally includes a method for intraoperative imaging. The method includes acquiring a background image of a target tissue, and activating a light-emitting diode. The method further includes acquiring an excitation image of the target tissue illuminated by the light-emitting diode, the excitation image corresponding to an excitation state of the light-emitting diode. Additionally, the method includes acquiring a calibration image of the target tissue illuminated by the light-emitting diode, the calibration image corresponding to a steady-state of the light-emitting diode. The method includes acquiring a decay image of the target tissue illuminated by the light-emitting diode, the decay image corresponding to a decay state of the light-emitting diode. The method further includes calculating a total signal image based on the background image, the excitation image, the calibration image, and the decay image.

In some embodiments, the light-emitting diode can remain in the excitation state for 1 to 10 nanoseconds. Additionally, the method can include generating a relative lifetime map of the target tissue using the total signal image. The method can include displaying the relative lifetime map in real-time. In some embodiments, the method can include identifying an abnormal portion of the target tissue via the relative lifetime map. Further, in some embodiments, the background image can be acquired when the light-emitting diode is not activated.

The present disclosure additionally includes a method for imaging tissue. The method includes illuminating a target tissue via a light-emitting diode. The method further includes acquiring a plurality of timed images of the target tissue including an excitation image corresponding to an excitation state of the light-emitting. Additionally, the method includes generating a relative lifetime map of the target tissue based on the plurality of timed images.

In some embodiments, the plurality of timed images of the target tissue includes a calibration image corresponding to a steady-state of the light-emitting diode, a decay image corresponding to a decay state of the light-emitting diode, and a background image corresponding to an inactive state of the light-emitting diode. In some embodiments, the plurality of timed images can be acquired by imaging the target tissue in vivo.

BRIEF DESCRIPTION OF THE DRAWINGS

FIG. 7 is a table of lifetime analysis results, in accordance with aspects of the present disclosure.

DETAILED DESCRIPTION

Figure 1:
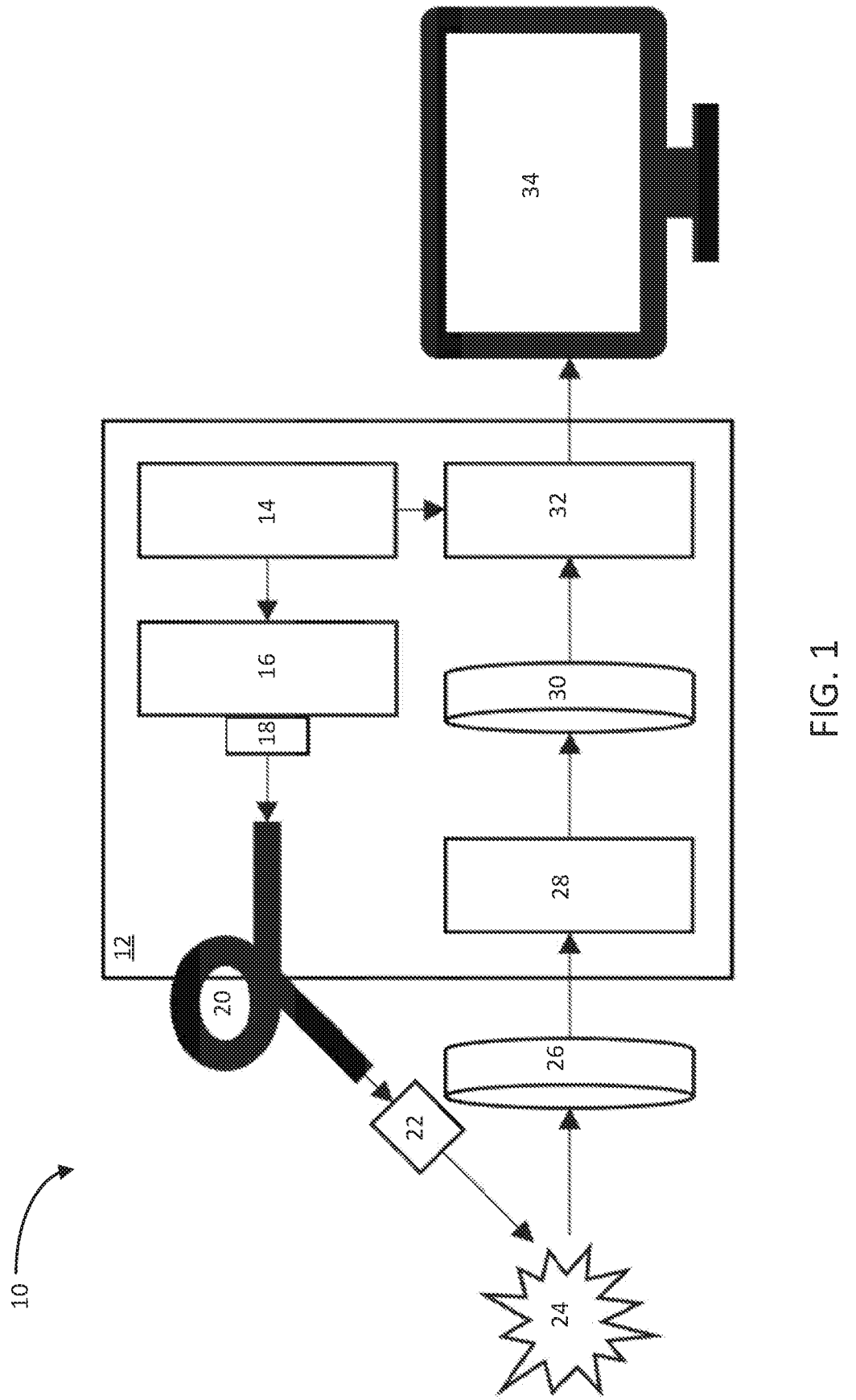
FIG. 1 is a block diagram of an imaging system in accordance with aspects of the present disclosure.

The following systems and methods address one or more of the aforementioned problems and provides additional advantages. As will be described, an imaging system is provided that can be configured for intraoperative use. In some aspects, the system allows for clinically meaningful contrast imaging to occur in near real-time.

As described above, the success of oncologic head and neck surgery can depend on the sensitivity with which tumor and vital tissue can be intraoperatively detected. During an operation, the surgeon may rely on white light reflectance, their tactile senses, and/or intermittent tissue biopsy with rapid frozen section pathology. Accuracy can vary widely based on the experience of the surgeon, the pathologist, and the location and type of tumor. In addition, efficacy is confounded by limitations on the extent of resection due to risks of damage to adjacent vital structures. The lack of any standard technology applied in the field of head and neck oncology to enhance intraoperative margin control creates a pressing medical need.

Preoperative imaging can be used to assess tumor size and extent, however, intraoperative margin detection relies solely on visual and tactile feedback during surgical resection. Concurrent to the operation, pathologists aid in tumor localization via the preoperative assessment of margins via frozen section microscopy. In total, the decision to end the resection or further extend margins is based on preoperative imaging studies, the visual and tactile acuity of the surgeon, and the spot biopsy-dependent results of frozen section pathology.

Concerning optical approaches, fluorescence lifetime imaging (FLIM) has demonstrated potential value for functional imaging. FLIM is a technique where the autofluorescence of a sample is probed in both the wavelength and time domains by excitation of the sample with a short optical pulse. Subsequently, the autofluorescence lifetime of tissue is detected at a range of different wavelengths. Lifetimes are dependent on the intrinsic biochemical composition of the targeted material and significant contrast can be generated by mapping the measured decays into an image. Thus, some advantages of FLIM are that time-resolved fluorescence is invariant to obscurants in the surgical field (e.g., blood, sweat, hair, etc.) and surfaces defined by complex geometries. In addition, fluorophore lifetimes are often strongly dependent on conditions related to occurring physiological processes, (e.g., oxygenation, pH, and temperature).

In order to generate functional tissue contrast via lifetime imaging, dynamic optical contrast imaging (DOCI) may be used. The general basis of tissue contrast in DOCI is due to biochemical, metabolic (i.e. altered concentrations of NADH and FAD), and structural changes that alter the emission properties of cancerous tissue. Broadly, DOCI is a technique that seeks to generate contrast from relative differences in fluorophore lifetimes without the need to compute absolute lifetime values. In particular, DOCI is an imaging technique that generates image contrast through ratiometric measurements of the autofluorescence decay rates of aggregate fluorophores in tissue.

Advantageously, the mechanism of DOCI is non-invasive and does not require special dye or injection of exogenous contrast agents. Further, DOCI can enable better tissue characterization by utilizing wide-field signal integration, eliminating constraints of uniform illumination, and reducing time-intensive computations that are bottlenecks in the clinical translation of traditional fluorescence lifetime imaging.

Over the course of carcinogenesis, the contribution of NADH to fluorescence substantially rises. NADH has a short lifetime (~0.5 ns for unbound; ~1 ns for bound) and results in a decrease in fluorescence lifetime in malignant tissue. This indicates that biochemical changes in OSCC tissue gives rise to fluorophore lifetime related contrast that may be sufficient to discriminate OSCC from normal tissue.

Two of the most significant roadblocks preventing widespread implementation of fluorescence lifetime imaging as a commonplace clinical imaging modality are the high system cost and the acquisition of a minimum photon count that permits calculation of fluorescence lifetime in a photon starved environment. The presently disclosed imaging systems and methods permit the use of relatively inexpensive LEDs for illumination, and significantly reduces the cost of a system that can generate fluorophore lifetime based contrast. The present disclosure includes imaging systems and methods that do not rely on the use of any dye or exogenous contrast agent, while providing a surgically relevant large field of view and with real-time feedback to the surgeon.

Additionally, the present disclosure provides a doubling of DOCI signal levels. This may permit simultaneous imaging during surgical resection without the traditional need to turn off all the lights (and headlamps) in the operating room (due to an increase in acquired signal). The presently disclosed imaging systems and methods may significantly improve outcomes for patients by minimizing the removal of normal functional tissue and assist in the complete and rapid removal of diseased tissues. As will be described, the disclosed systems and methods enable intraoperative imaging capable of rapid tissue differentiation by generating fluorescence lifetime contrast at large, surgically relevant fields of view.

In some aspects, the present imaging system includes an integrated LED driver circuit. The LED driver circuit can improve and/or optimize the linear fall time from steady state illumination to between about 1-10 nanoseconds. The LED rise time can also be sufficiently linear, with a 1-10 nanosecond rise time that permits a new avenue to gather useful fluorescent contrast. Notably, conventional imaging methods discourage tissue differentiation based on fluorescent contrast during excitation, and teach that only fluorophore decay from an excited state contains contrast information unique to the fluorophores of a specimen. This common conclusion is understandable, since nearly every conventional application of fluorescence lifetime imaging utilizes an illumination source resembling an impulse function (e.g., via the use of a laser), or alternatively, is exponential in nature.

The presently disclosed systems and methods overcome the constraints of conventional imaging. In particular, the LED illumination within a DOCI system (as described herein) permits a nearly linear rise, steady-state, and falling intensity (with respect to time on the nanosecond order), as shown graphically in FIG. 4. Accordingly, fluorescence lifetime contrast is attainable when normalizing the sample fluorescence during both the rising and decaying time periods to a steady-state value. Thus, the present disclosure exploits two regions of useful contrast, in that a pulse sequence may be combined in order to effectively double the signal to noise ratio (e.g., by up to 40%) without incurring a reduction in imaging speed. According to aspects of the present disclosure, the dynamic range of signal can also be increased since it is possible to generate DOCI values as large as 2, compared to prior methods capped at a value of 1.

Referring now to FIG. 1, a block diagram of an imaging system 10 is shown, in accordance with aspects of the present disclosure. In some aspects, the imaging system 10 can include an enclosure 12. The enclosure 12 is shown to include a dual output function generator 14 in communication with a driver circuit 16, an LED 18 (e.g., emitting 365 nm light), and at least a portion of a liquid light guide 20. The enclosure 12 is shown to further include a lens 28, a motorized filter wheel 30, and an intensified charge-coupled device (iCCD) camera 32. In some aspects, the imaging system 10 can include a collimating lens 22, a tissue interface 24, and a UV filter 26. The tissue interface 24 shown in FIG. 1 can be representative of the excitation of endogenous fluorophores in tissue. In some aspects, the imaging system 10 can include a computer controller 34 (e.g., including a display).

Still referring to FIG. 1, the dual output function generator 14 can provides a trigger to the driver circuit 16. The driver circuit 16 can be configured to drive the LED 18 (e.g., a high-intensity, 365 nm LED) for illumination, and the iCCD camera 32 (e.g., a gated and intensified CCD camera) can be configured for image acquisition. In some instances, the iCCD camera 32 can be a commercially available iCCD camera, such as the Andor iStar cameras available from Oxford Instruments.

Light pulses from the LED 18 can travel through the liquid light guide 20, and can subsequently be collimated via the collimating lens 22 onto the tissue interface 24 (or other object of interest). Fluorescence can be detected by the lens 28 (e.g., a zoom lens) with the UV filter 26. In some aspects, the UV filter 26 can be used in conjunction with bandpass filters to further reject reflected UV illumination. Further, in some instances, the UV filter 26 can be a commercially available UV filter, such as the 405 nm longpass filter available from Edmund Optics®.

The motorized filter wheel 30 can include a plurality of bandpass filters, configured to obtain spectral information from the tissue (or other sample, object). As an example, the motorized filter wheel 30 can include ten bandpass filters. In some instances, the motorized filter wheel 30 can be a commercially available filter wheel, such as filter wheels available from Zaber Technologies. Additionally, in some instances, the bandpass filters can be commercially available, such as the bandpass filters available from Semrock. As an example, ten bandpass filters may be used with the motorized filter wheel 30, and respectively centered at: 407 nm, 434 nm, 465 nm, 494 nm, 520 nm, 542 nm, 572 nm, 605 nm, 652 nm, and 676 nm. Further, the bandpass filters may have a bandwidth of ~20 nm. In some aspects, the iCCD camera 32 and/or the motorized filter wheel 30 can be controlled by a user-developed software, enabling the imaging system 10 to rapidly acquire images at a preset number of wavelengths. In some aspects, the imaging system 10 can include additional components and/or features.

The computer controller 34 can facilitate the operation of the user-developed software, according to some aspects of the present disclosure. In some aspects, the computer controller 34 can include a display; one or more input devices, such as a keyboard and mouse; and a computer processor. The computer processor may include a commercially available programmable machine running a commercially available operating system. In general, the computer controller 34 can be in communication with a data store server. By way of example, the computer controller 34 and data store server 230 may be connected via a communication system, which may include any suitable network connection, whether wired, wireless, or a combination of both. As an example, the communication system may include both proprietary or dedicated networks, as well as open networks, such as the internet.

Figure 2:
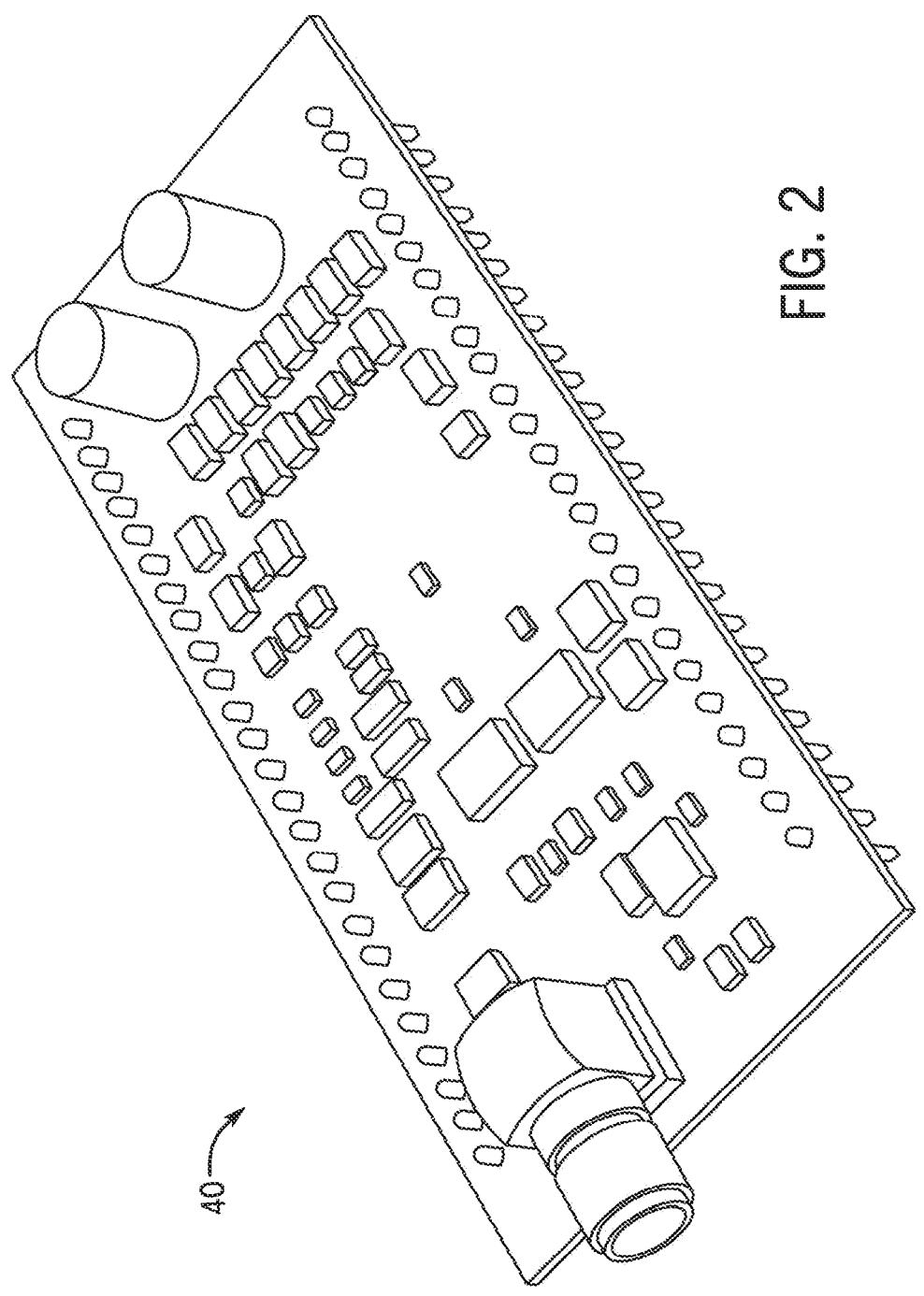
FIG. 2 is an example printed circuit board corresponding to the imaging system of FIG. 1, in accordance with aspects of the present disclosure.
Figure 3:
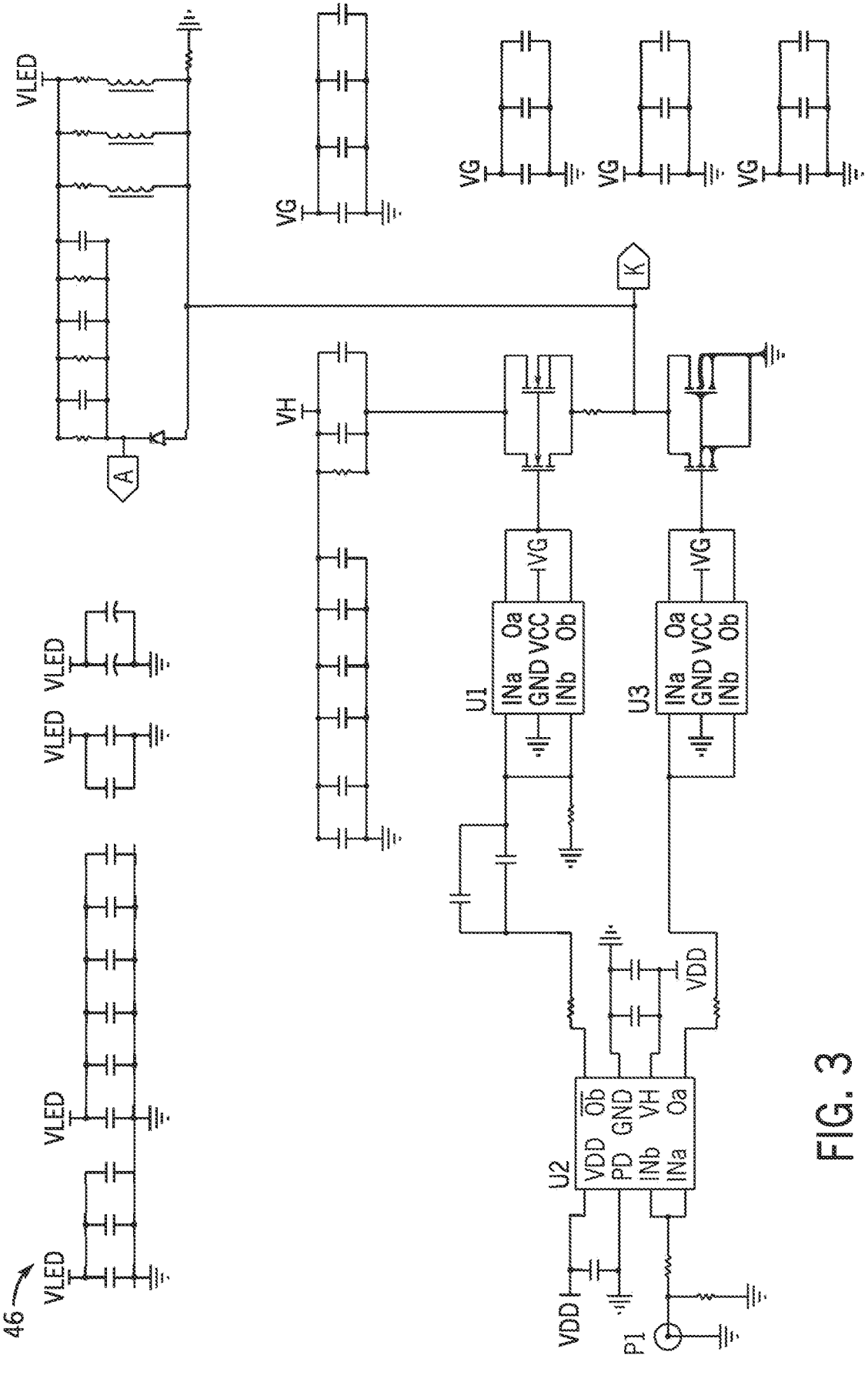
FIG. 3 is an example circuit diagram corresponding to the printed circuit board of FIG. 2.

Referring now to FIGS. 2-3, an example printed circuit board (PCB) 40 (see, e.g., FIG. 2) and a corresponding circuit diagram 46 (see, e.g., FIG. 3) are shown, according to aspects of the present disclosure. In some aspects, the PCB 40 may be implemented within the imaging system 10 (e.g., as driver circuit 16). The PCB 40 can be configured to drive the LED (e.g., LED 18) to produce the desired illumination pulse profile.

In some aspects, the imaging system 10 can include an imaging algorithm. The imaging algorithm can illuminate the target (e.g., the tissue interface 24) with a linear or nearly linear excitation pulse of light that can increase in intensity (10-90%) over the time of 1-10 nanoseconds. A calibration image of the target can be acquired once steady-state is reached via optical pumping of the fluorophores (e.g., via LED 18). This calibration image can include fluorescence values from the emissions of the excited fluorophores of the target. Additionally, a background image of the target can be acquired, during which the LED (e.g., LED 18) is turned off and not emitting any light. This background image can be subtracted from the calibration image in order to account for ambient light or optical noise in the area of imaging. An excitation image of the target can be acquired, including the fluorescence values during excitation towards steady state from ground state as the emissions of the sample increase from dark to bright. A decay image of the target can be acquired, including the fluorescence values during decay from steady state towards ground state as the emissions of the sample decrease from bright to dark.

Still referring to the imaging algorithm, addition of a second term, namely (calibration image-excitation image)/(calibration image-background image) can be added to the first original term, (decay image-background)/(calibration image-background), in order to produce a total signal image, maximizing signal to noise and dynamic range, thus producing superior image contrast by harnessing additional signal from the targeted sample. The subtraction of the background image accounts for ambient and stray light in the environment. The total signal image is a relative lifetime map of the target. Using values in the relative lifetime map, one can identify a boundary between a first group of cells or cell products having a first physiologic process and a second group of cells or cell products having a different physiologic process. The mathematical operations for each pixel that involve the sources of contrast can be provided by Equation 1:

$$\text{Signal per pixel} = \frac{\int_{C}^{D} f(x)dx - \text{background}}{\int_{B}^{C} f(x)dx - \text{background}} + \frac{\int_{B}^{C} f(x)dx - \int_{A}^{B} f(x)dx}{\int_{B}^{C} f(x)dx - \text{background}} \quad (1)$$

where x is the detector photon count (or proportional value to photon count) at each pixel.

Comparatively, an earlier described DOCI calculation method (where signal is only acquired from the decay image) can be provided by Equation 2:

$$\text{Signal per pixel} = \frac{\int_{C}^{D} f(x)dx - \text{background}}{\int_{B}^{C} f(x)dx - \text{background}} \quad (2)$$

The array of generated pixel values can serve as a lifetime map for the clinician and may immediately be presented in order to guide the physician in clinic or surgery. The clinician may infer physiologic and pathologic processes occurring, based on information presented by the system in order to screen patients, choose the best location for tissue biopsy, identify noncontiguous areas of pathology, identify incomplete resection, and conduct faster margin analysis (when compared to conventional histopathology).

Figure 4:
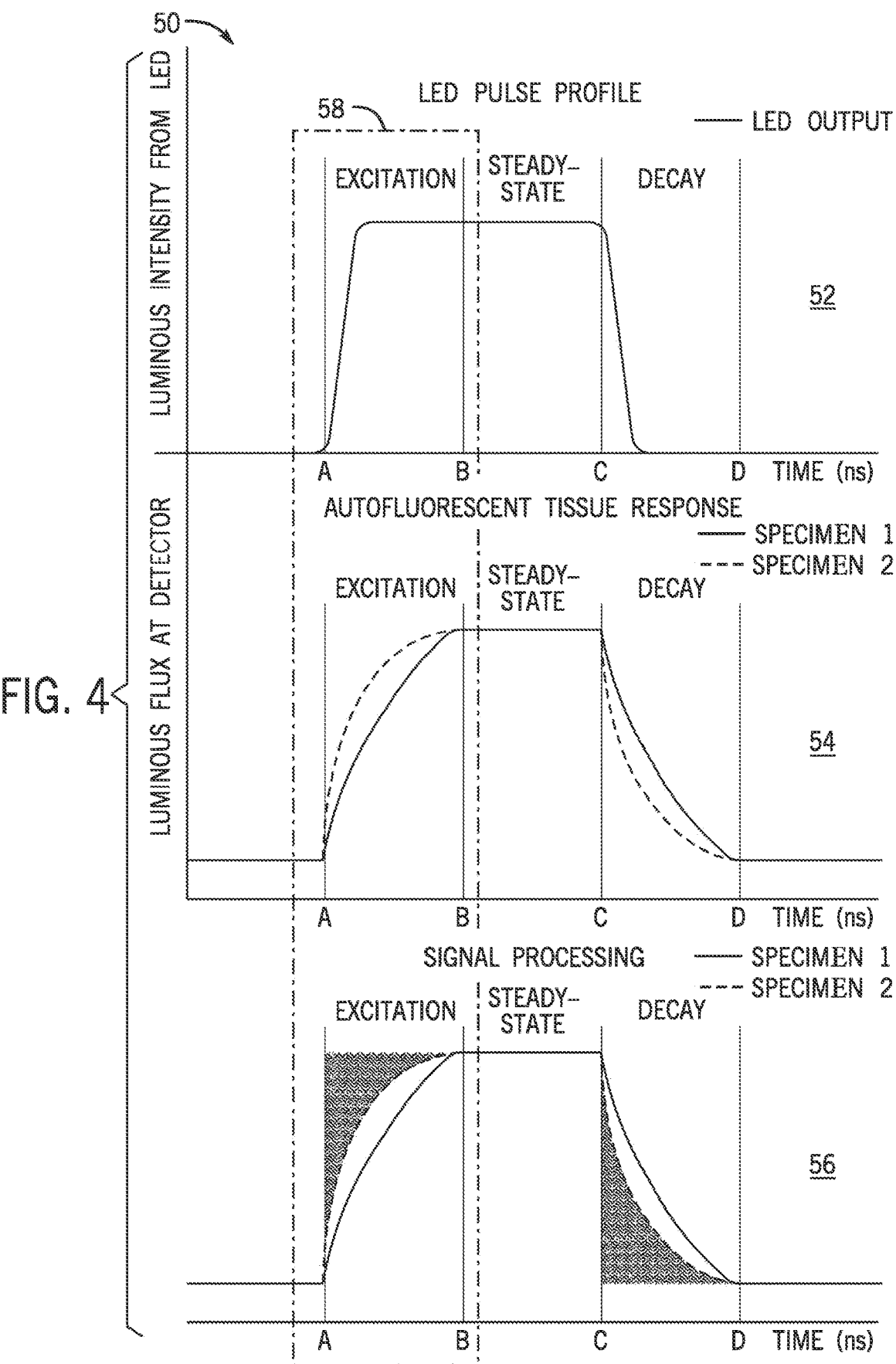
FIG. 4 is a series of graphs representative of data sampling for increased signal to noise ratio, in accordance with aspects of the present disclosure.

Referring specifically to FIG. 4, a series 50 of graphs (52, 54, 56) representative of an imaging algorithm (e.g., as described above) is shown, according to aspects of the present disclosure. As shown, graph 52 illustrates an LED pulse profile that includes the luminous intensity from the LED (e.g., LED 18) over time. Three segments of the LED pulse profile are identified across each of graphs 52, 54, 56: excitation, steady-state, and decay. The various segments are indicated via x-axis markers A-D.

FIG. 4 graphically represents an improved signal in that the information gained during rise time can be used to augment the fall time information. Using both rise and fall time information means that the DOCI values are bound between 0 (very short lifetime) and 2 (very long lifetime). Note that the background term is evaluated as the average detected signal in which no fluorescence is occurring, i.e., before excitation or after all excitation ceases. The time increment for measurement of rise, steady state, fall, and background is assumed to be constant, and the background is assumed to not change during the period of data gathering. If, for some reason, the measurement time increments are not equal, then each of these values can be multiplied by appropriate scaling.

Graph 54 (of FIG. 4) illustrates an autofluorescent tissue response that includes the luminous flux determined at the detector, over time. The source of the luminous flux results from the convolution of the fluorescence response function of the aggregate excited fluorophores in the region of interest and the incident light pulse from the LED onto these fluorophores. Notably, the results for two specimens are shown via graph 54. Further, graph 56 illustrates signal processing corresponding to Equation 1, as described above.

Referring to the series 50, the prior DOCI method (see, e.g., Equation 2) generates signal by integrating the area under the curve between points C-D for either specimen #1 (longer aggregate fluorophore fluorescence lifetime) or specimen #2 (shorter aggregate fluorophore fluorescence lifetime), respectively. Region 58 highlights the new source of lifetime contrast (generated during sample excitation) that the present disclosure harnesses. In some aspects, the present disclosure can provide a 40% increase in overall signal to noise, without an increase in imaging time.

Figure 10:
FIG. 10 is a flowchart illustrating a process for calculating a total signal image, in accordance with aspects of the present disclosure.
Figure 10:
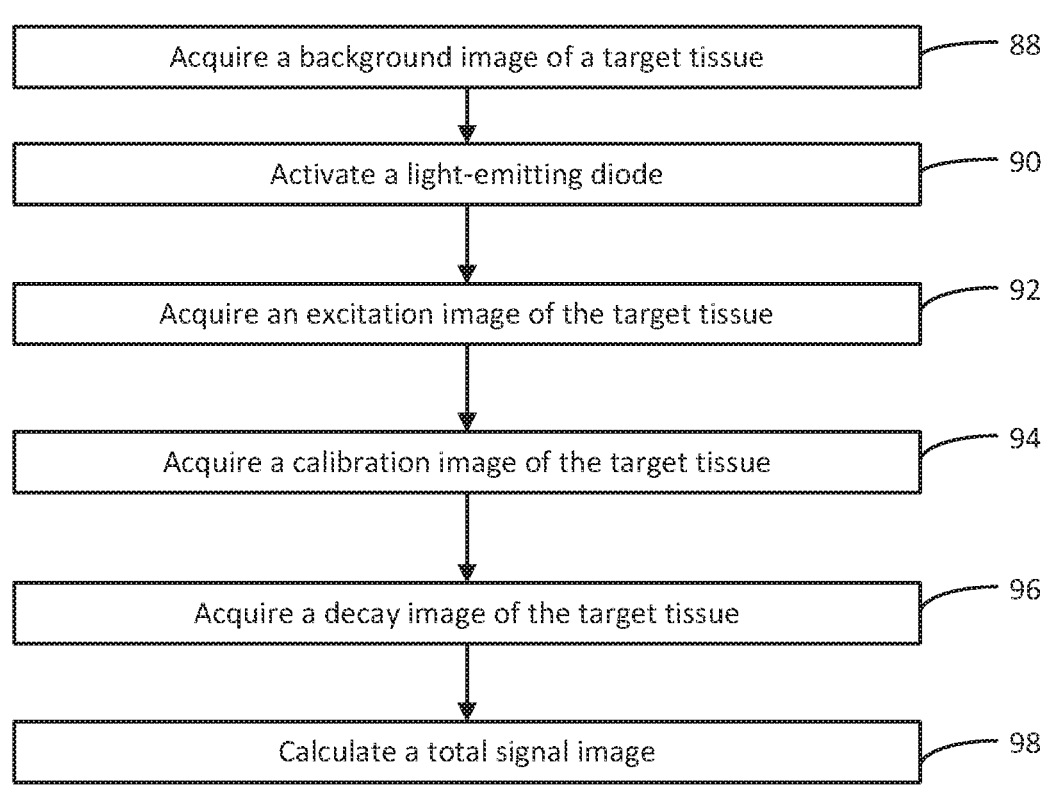

Referring to FIG. 10, a process 86 for generating a total signal image is shown, according to some embodiments. The process 86 can include acquiring a background image of a target tissue (process step 88), and activating a light-emitting diode (process step 90). The process 86 is additionally shown to include acquiring an excitation image of the target tissue (process step 92), acquiring a calibration image of the target tissue (process step 94), and acquiring a decay image of the target tissue (process step 96). The process 86 can further include calculating a total signal image (process step 98). The process 86 can include additional, or fewer steps, according to some embodiments.

Figure 11:
FIG. 11 is a flowchart illustrating a process for generating a relative lifetime map, in accordance with aspects of the present disclosure.
Figure 11:
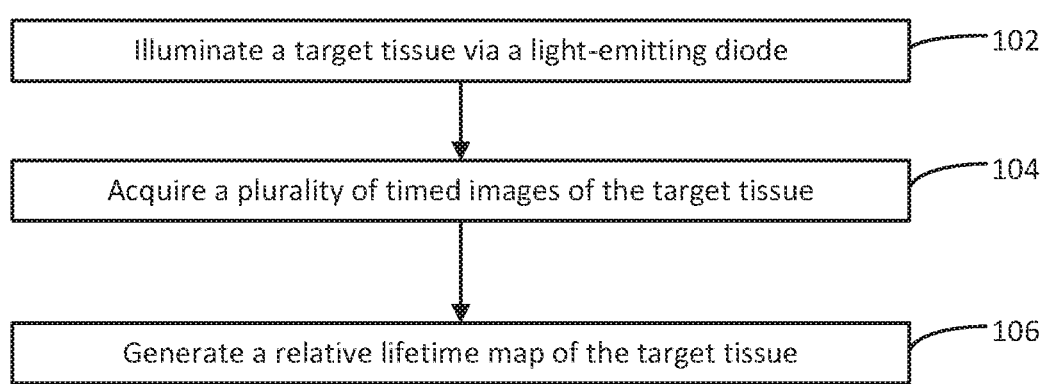

Referring to FIG. 11, a process 100 for generating a relative lifetime map is shown, according to some embodiments. The process 100 can include illuminating a target tissue via a light-emitting diode (process step 102). The process 100 can further include acquiring a plurality of timed images of the target tissue (process step 104). The process 100 can additionally include generating a relative lifetime map of the target tissue (process step 106). The process 100 can include additional, or fewer steps, according to some embodiments.

EXAMPLES

Aspects of the imaging system 10 and associated methods were evaluated. The optical response of the LED was measured using the Andor iStar 334T camera. Spatial resolution was determined using a fluorescent 1951 USAF target (from Edmund Optics®) with peak excitation at 365 nm and peak emission at 550 nm. The filters were individually tested using a compact spectrometer (Thorlabs CCS200) with extended range (200-1000 nm) and accompanying Thorlabs OSA software for PC. The spectra from each filter was normalized and plotted altogether using Matlab 2019$b$ (Mathworks) with custom written code.

Stock solutions of NADH, Laurdan, and 7-hydroxy-4-methylcoumarin were prepared as detailed in table 76 of FIG. 7. The stock solutions were then split. One half of each solution was taken to the experimental DOCI system and imaged while the other half was imaged by a commercial Leica SP8 MP-DIVE system with FLIM extension. 100 microliter samples of each dye were pipetted into open top 12-well slides and excited with a femtosecond pulsed laser at 730 nm for two photon occurrence at approximately the same 365 nm emission of the LED in the DOCI system. The SP8 microscope used a Leica HC PL FLUOTAR 10×/0.40 CS2 Dry objective and HyD detector. The Leica HyD detector was configured with a 408-550 nm bandpass filter while the DOCI system utilized a 405 long-pass filter, thus solely filtering out the illuminating wavelengths of light. Fluorescence lifetimes for each dye were determined at multiple concentrations using the fit-free phasor module of the Las X (Leica) software with n-exponential autofitting enabled. Results were analyzed for linearity using Prism 8 (Graphpad) for Mac OS by creating a best-fit-line with simple linear regression.

An adenomatous parathyroid gland was immediately imaged with the DOCI system following surgical resection and subsequently imaged with the Leica MP-DIVE system previously described. Five, 200 micrometer size tiles were fused together with the Las X software and lifetime values were similarly determined using the phasor module of the Leica system.

Figure 5:
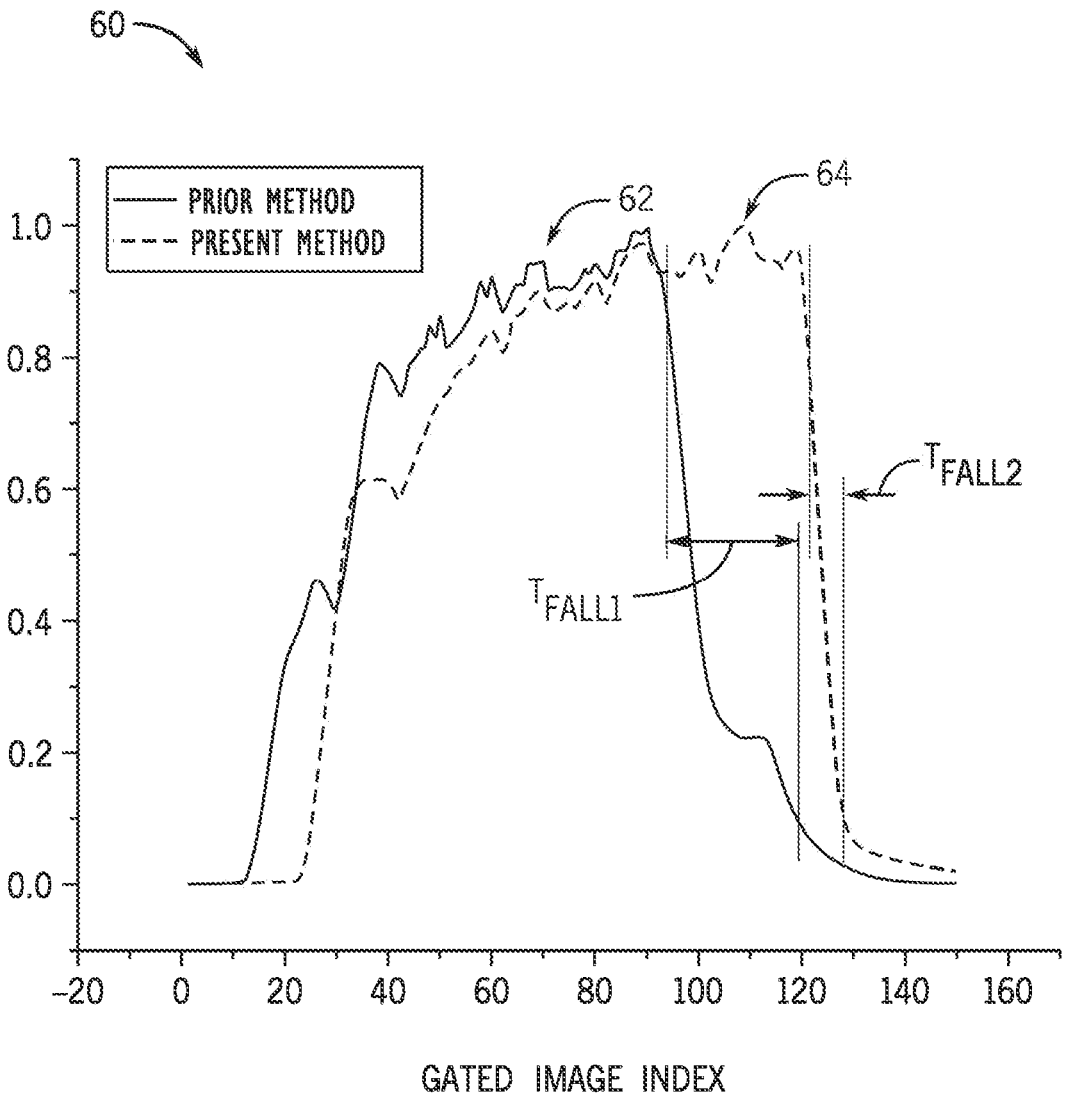
FIG. 5 is a graph of optical response test results, in accordance with aspects of the present disclosure.

Referring to FIG. 5, the optical responses of the present LED and driver circuit board are compared to those of a prior system, in accordance with aspects of the present disclosure. A graph 60 includes a trace 62 corresponding to the optical pulse profile of the prior system, as well as a trace 64 corresponding to the optical pulse profile of the presently disclosed systems and methods. The integration time of each frame was 2 ns. Significantly, the fall time of the present system decreased with a four-fold improvement over the prior system. The decay profile of the present system accurately fits the mathematical model for calculating fluorescence lifetime contrast, and greatly facilitates image post-processing.

Figure 6:
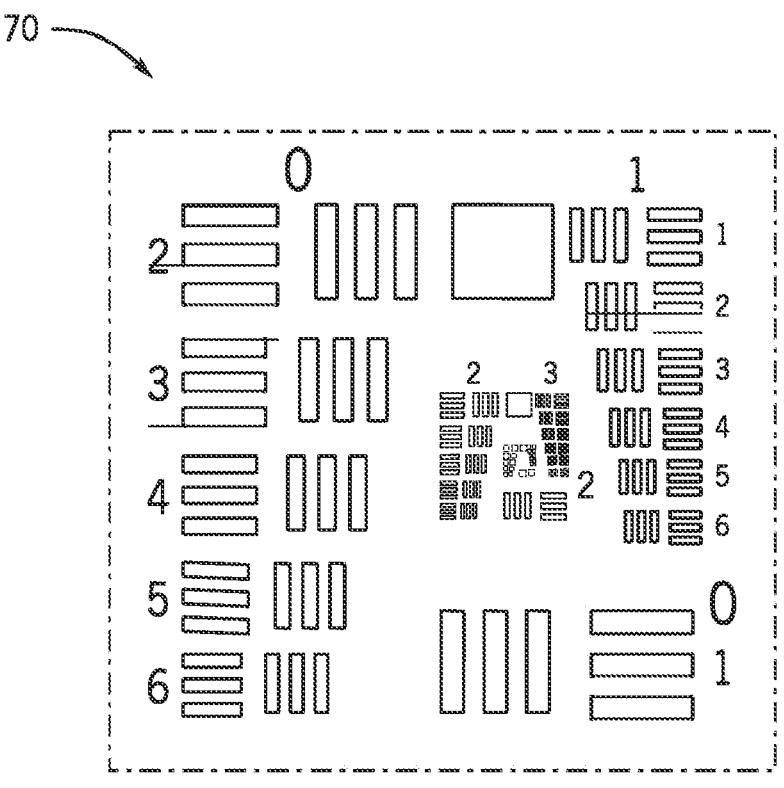
FIG. 6 is an image demonstrating an example spatial resolution and field of view, in accordance with aspects of the present disclosure.

Spatial resolution was determined using a fluorescent USAF target that was illuminated by the 365 nm LED in the DOCI system. The large 2×2 cm field of view 70 is demonstrated in via FIG. 6. The maximal horizontal and vertical resolution are both 7.13 micrometers since the sixth elements of the second group are the last distinguishable bars in the target. In summary, the fluorescent USAF test target defines a macroscopic field of view with sub millimeter resolution of 2×2 cm.

In order to validate the present method, the components and resolution of the present imaging system were evaluated. The quantitative output was also standardized against the fluorescence lifetime values of three dye standards with monoexponential decay using a commercial Leica two-photon fluorescence lifetime imaging microscope. Significantly, the present system continued to demonstrate clinically meaningful contrast between tissue samples with multiexponential decay.

Dye solutions were prepared in order to quantitatively verify the concordance between the ratiometric DOCI values (i.e., between 0 and 1) and actual fluorescence lifetime measurements on the picosecond scale. Phasor analysis demonstrated monoexponential decay for each dye. The results are reported in table 76 (FIG. 7). Analysis of DOCI system response is displayed in FIGS. 8A-8B via linear regression and line of best-fit. Notably, the results from dye standardization demonstrate high linear correlation between single exponential fluorescence lifetimes with DOCI values.

Figure 8B:
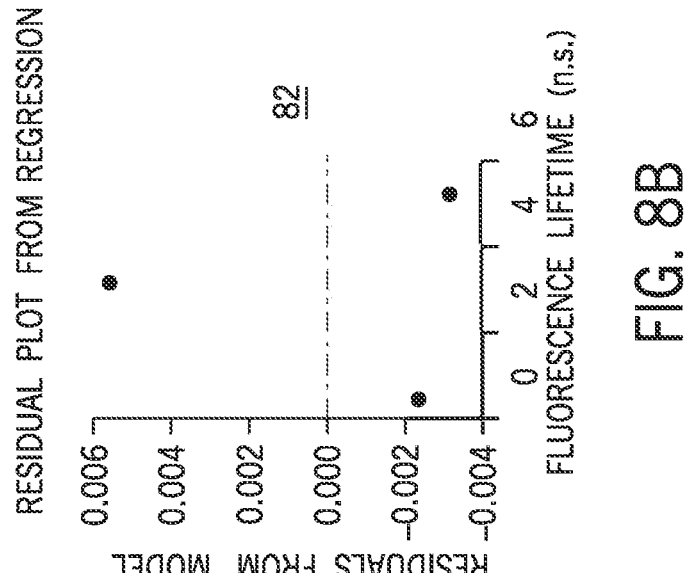
FIG. 8B is a residual plot from simple linear regression, in accordance with aspects of the present disclosure.
Figure 8A:
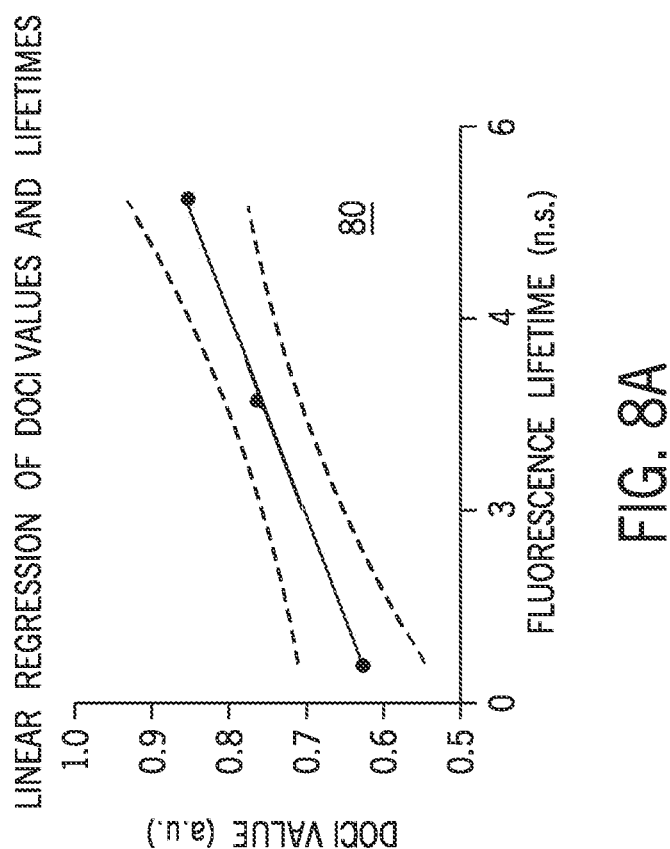
FIG. 8A is a linear regression plot of dynamic optical contrast imaging (DOCI) values and lifetimes, in accordance with aspects of the present disclosure.

Referring to FIGS. 8A-8B, graphs 80 and 82 are shown, according to aspects of the present disclosure. Accuracy of DOCI ratiometric values are compared to a Leica commercial microscope via simple linear regression. Graph 80 is shown to include the linear regression of DOCI values and lifetimes from the Leica system. The dashes lines represent 95% confidence interval for the best-fit line shown in solid. Graph 82 is shown to include a plot of residuals from the simple linear regression.

Figure 9:
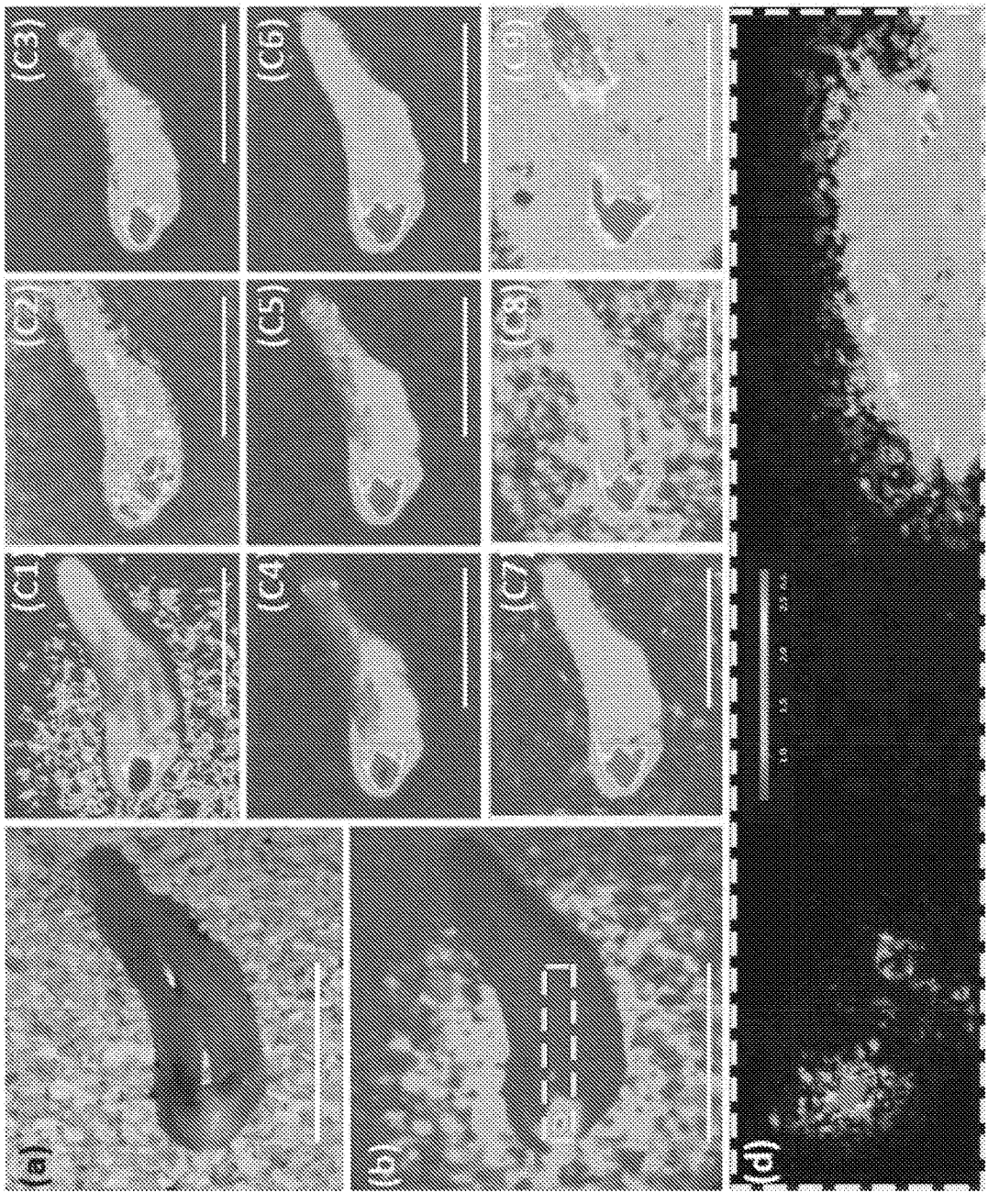
FIG. 9 is an image demonstrating the temporal resolution of a DOCI system referenced against a conventional imaging system, in accordance with aspects of the present disclosure.

Referring now to FIG. 9, clinical validation of the DOCI system accuracy is shown via the lifetime comparison of ex vivo human tissue, in accordance with aspects of the present disclosure. Resected parathyroid adenoma was imaged with the DOCI system after 15 minutes following excision due to transport of tissue from the operating room to the DOCI system. Each DOCI lifetime image (C1-C9 in FIG. 9) was generated in ~1 second and immediately displayed. Imaging with the Leica system was performed next with approximately 5 minutes transport time to the imaging location. Five, 200 micrometer images were fused together with phasor analysis generating lifetime values over a 2 hour time.

The DOCI system clearly demonstrates contrast between the parathyroid gland and adjacent fat, which differ in lifetime of around 1 nanosecond (FIG. 9—image "d"). Image "a" of FIG. 9 shows the parathyroid gland and adjacent fat; image "b" of FIG. 9 shows fluorescence intensity of the parathyroid and adjacent fat (taken via video mode of DOCI system); images "C1"-"C9" of FIG. 9 show the DOCI relative lifetime of the parathyroid and adjacent fat with different filters; image "d" of FIG. 9 shows the fluorescence lifetime taken with commercially available FLIM microscope, Leica Deep In Vivo Explorer SP8 DIVE (scale bar 1 cm).

The presently disclosed systems and methods augment signal-to-noise in a photon starved environment by using an LED instead of a laser for excitation, a large numerical aperture lens for detection, and wide bins for signal integration on a CCD detector. The spatial resolution of the example DOCI system was 7 micrometers while the residuals of the DOCI values against the actual fluorescence lifetimes suggested the temporal resolution of the system was well under 1 nanosecond. Thus, the present disclosure generated highly accurate and clinically useful images within seconds at a drastically reduced cost (i.e., <$50,000, compared to the ~$1.3M Leica SP8 DIVE system). Further, the Leica SP8 DIVE system required two hours of time to produce a micrometer thin cross-section of lifetime values with an order of magnitude smaller field of view. In summary, the presently disclosed systems and methods demonstrate clinically meaningful contrast in near real-time based on aggregate endogenous fluorescence lifetime.

Alternative embodiments are expressly contemplated. In one alternative embodiment, a single detector may be used to acquire the signal in two separate passes. During the first scan, fluorescent intensity can be collected by a first gate in the interval A-B (see FIG. 4). The information can then undergo analog-to-digital conversion and readout to a computer. A second gate can operate in the interval C-D (see FIG. 4), after which information can similarly undergo analog-to-digital conversion and readout to the computer.

In another alternative embodiment, two detectors can be used to simultaneously acquire signal, the two detectors properly synced via a timing pulse. This arrangement splits the two scan workload to permit simultaneous scan acquisition. Thus, the necessary time of acquisition will be half that of the alternative embodiment involving a single detector.

In a third alternative embodiment, use of a Field Programmable Gated Array (FPGA) can integrate the signal in real-time (as it is acquired from the detector), perform mathematical operations, and directly read out DOCI lifetime values (which can be displayed graphically to a user). This arrangement may be limited solely by the rate of camera data readout to the computer. However, a benefit is integrated computation and direct readout of the final DOCI lifetime values to the computer. Thus, there would not be a need to perform simple mathematical operations on the computer, and real-time lifetime imaging is more feasible.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. Various features and advantages of the invention are set forth in the following claims.

What is claimed is:

1. A system for intraoperative imaging, the system comprising:
   a camera;
   a light-emitting diode; and
   a processor in communication with the camera and the light-emitting diode, the processor configured to:
      illuminate a target tissue via the light-emitting diode;
      acquire, via the camera, a plurality of timed images of the target tissue including multiple excitation images acquired during an excitation state of the light-emitting diode and multiple decay images acquired during a decay state of the light-emitting diode; and
      generate a relative lifetime map of the target tissue based on the plurality of timed images.

2. The system of claim 1, wherein the plurality of timed images further comprises a calibration image and a background image, the calibration image corresponding to a steady-state of the light-emitting diode and the background image corresponding to an average detected signal when the light-emitting diode is not illuminated.

3. The system of claim 2, wherein the processor is configured to generate the relative lifetime map by calculating a total signal image, and wherein:

$$\text{total signal image} = \frac{(\text{calibration image} - \text{excitation image})}{(\text{calibration image} - \text{background image})} +$$

12

$$\frac{(\text{decay image} - \text{background image})}{(\text{calibration image} - \text{background image})}.$$

4. The system of claim 1, wherein the excitation state of the light-emitting diode occurs for 1 to 10 nanoseconds.

5. The system of claim 1, wherein the processor is configured to acquire the plurality of timed images while background lighting is delivered to the target tissue from a lighting source that is distinct from the light-emitting diode.

6. The system of claim 1, wherein the processor is configured to acquire the plurality of timed images and generate the relative lifetime map in real-time.

7. The system of claim 1, wherein the relative lifetime map includes a boundary on the target tissue, the boundary identifying cells having a first property from cells having a second property.

8. The system of claim 7, wherein the first property corresponds to cells having a first physiologic process and the second property corresponds to cells having a second physiologic process.

9. The system of claim 1, further comprising a user display in communication with the processor, wherein the processor is further configured to output the relative lifetime map to the user display.

10. The system of claim 1, wherein the processor is configured to illuminate and acquire the plurality of timed images of in-vivo tissue.

11. A method for intraoperative imaging, the method comprising:
   acquiring a background image of a target tissue;
   activating a light-emitting diode;
   acquiring multiple excitation image, §, of the target tissue illuminated by the light-emitting diode, wherein the excitation images are acquired during an excitation state of the light-emitting diode;
   acquiring a calibration image of the target tissue illuminated by the light-emitting diode, the calibration image corresponding to a steady-state of the light-emitting diode;
   acquiring multiple decay images of the target tissue illuminated by the light-emitting diode, wherein the decay image are acquired during a decay state of the light-emitting diode; and
   calculating a total signal image based on the background image, the excitation images, the calibration image, and the decay images.

12. The method of claim 11, wherein calculating the total signal image comprises:

$$\text{total signal image} = \frac{(\text{calibration image} - \text{excitation image})}{(\text{calibration image} - \text{background image})} +$$

$$\frac{(\text{decay image} - \text{background image})}{(\text{calibration image} - \text{background image})}.$$

13. The method of claim 11, wherein the light-emitting diode remains in the excitation state for 1 to 10 nanoseconds.

14. The method of claim 11, further comprising generating a relative lifetime map of the target tissue using the total signal image.

15. The method of claim 14, further comprising displaying the relative lifetime map in real-time.

16. The method of claim 14, further comprising identifying an abnormal portion of the target tissue via the relative lifetime map.

17. The method of claim 11, wherein the background image is acquired when the light-emitting diode is not activated.

18. A method for imaging tissue, the method comprising:

illuminating a target tissue via a light-emitting diode;

acquiring a plurality of timed images of the target tissue including multiple excitation images acquired during an excitation state of the light-emitting; and generating a relative lifetime map of the target tissue based on the plurality of timed images.

19. The method of claim 18, wherein the plurality of timed images of the target tissue includes:

a calibration image corresponding to a steady-state of the light-emitting diode;

a decay image corresponding to a decay state of the light-emitting diode; and a background image corresponding to an inactive state of the light-emitting diode.

20. The method of claim 19, wherein the relative lifetime map corresponds to a total signal image, and wherein:

$$\text{total signal image} = \frac{(\text{calibration image} - \text{excitation image})}{(\text{calibration image} - \text{background image})} + \frac{(\text{decay image} - \text{background image})}{(\text{calibration image} - \text{background image})}.$$

21. The method of claim 18, wherein the plurality of timed images are acquired by imaging the target tissue in vivo.

*   *   *   *   *